United States Patent [19]

Fujiwara et al.

[11] 4,295,949
[45] Oct. 20, 1981

[54] METHOD FOR DETERMINING BOUNDARY POINTS IN ELECTROPHORESIS

[75] Inventors: Toshihide Fujiwara, Fuchu; Ryo Fujimori, Hachiouji, both of Japan

[73] Assignee: Olympus Optical Co., Ltd., Tokyo, Japan

[21] Appl. No.: 151,889

[22] Filed: May 21, 1980

[30] Foreign Application Priority Data

May 25, 1979 [JP] Japan ................... 54-64814

[51] Int. Cl.$^3$ ............................................. G01N 27/26
[52] U.S. Cl. ............................ 204/180 G; 204/180 S; 204/299 R
[58] Field of Search ........... 204/180 G, 180 S, 180 R, 204/299 R

[56] References Cited

U.S. PATENT DOCUMENTS

| | | | |
|---|---|---|---|
| 3,096,137 | 7/1963 | Silaro | 356/201 X |
| 3,399,127 | 8/1968 | Rand et al. | 204/180 G |
| 3,459,948 | 8/1969 | Cosci | 356/203 X |
| 3,649,498 | 3/1972 | Pretorius et al. | 204/180 G |
| 3,912,609 | 10/1975 | Arlinger | 204/180 R |

*Primary Examiner*—Arthur C. Prescott
*Attorney, Agent, or Firm*—Cushman, Darby & Cushman

[57] ABSTRACT

A method for determining boundary points in electrophoresis comprising a step to determine points on the abscissa corresponding to peak tops on a densitogram traced on the basis of electrophoresis of a standard sample as standard positions, a step to locate positions corresponding to said standard positions on a densitogram traced on the basis of electrophoresis of an unknown sample, a step to determine the point corresponding to the lowest concentration among points having minimum values between each pair of neighboring standard positions as the normal boundary point and a step to calculate an integral or a value proportional to the integral of each fraction delimited by the boundary points thus determined.

5 Claims, 9 Drawing Figures

016,949

METHOD FOR DETERMINING BOUNDARY POINTS IN ELECTROPHORESIS

BACKGROUND OF THE INVENTION

1. Field of the Invention

The present invention relates to a method for processing fractionated patterns of serum formed by the electrophoresis.

2. Description of the Prior Art

FIG. 1 shows a basic pattern of concentration distribution on fractionated patterns formed by electrically energizing with an electrophoretic apparatus a carrier made of cellurose acetate film onto which man's serum is applied (a healthy man's serum generally shows this pattern). Such an electrophoretic patterns usually consists of five fractions of A, B, C, D and E including five peaks of $a_0$, $a_1$, $a_2$, $a_3$ and $a_4$ corresponding to albumin (A), alpha 1 globulin (B), alpha 2 globulin (C), beta globulin (D), and gamma globulin (E) respectively. Diagnosis or distinguishment between normality and abnormality is done on the basis of an analog diagram and values in percentage of the respective fractions. However, patterns of concentration distribution on fractionated patterns of actual sample may include peaks produced by various causes in addition to those shown in FIG. 1. The pattern illustrated in FIG. 2, for example, include a peak designated as $a_5$ in addition to the five peaks mentioned above. This peak is produced due to turbidity in serum which allows a substance insensible of electrophoresis to remain at the position of sample application. The electrophoretic pattern shown in FIG. 3 includes an additional peak at the position of $a_6$, whereas the one shown in FIG. 4 includes an additional peak at the position of $a_7$. These peaks are produced by fractionation of certain components contained in sera depending on their freshness, the additional peak shown in FIG. 3 being produced by beta lipoprotein and that in FIG. 4 being produced by $\beta_{1c}$ globulin.

When colorimetry is done on a sample which shows peaks in addition to the five basic peaks, inconvenience is caused in automatic processing with a computer of data obtained by colorimetry. FIG. 5 shows an example of configuration of a densitometer and a photometric apparatus which are currently employed. In the block diagram shown in FIG. 5, the light emitted from a light source lamp 3 is passed through a lens 4, a filter 5 and a slit 6, used for irradiating a carrier 1 (described later) and detected with a photo detector element 7. The carrier 1 has fractionated patterns 2, 2', 2", . . . of sera formed thereon as shown in FIG. 6, and is placed between the light source and the detector for photometry of the individual fractionated patterns while scanning in the direction perpendicular to the shifting direction of the carrier. That is to say, the light emitted from the light source lamp and passing through the sample (fractionated pattern of a serum) is received by the photo detector element 7, whose output corresponding to sample concentration is amplified with a preamplifier 8, converted by a logarithmic converter 9 into a logarithmic value and used for preparing an analog densitogram as shown in FIG. 1. Successively, output from the logarithmic converter 9 is inputted into an A/D converter 10 and converted into a digital signal by operating a conversion command signal generator 11 with a photometry command 11a from a computer 12. Value of each fraction is determined on the basis of the digital data obtained at this stage.

For the operations described above, it is sufficient to determine points of local minimum values as boundary points in such a case as shown in FIG. 1. In cases of the electrophoretic densitograms divided into more than five fractions as illustrated in FIG. 2 through FIG. 4, however, it is impossible to determine values of the five fractions. In a case where an electrophoretic densitogram has more than five fractions, it is therefore required for the analyst to check an analog pattern and electrophoretic pattern for recalculation through processing to attribute the additional peaks to any one of the areas corresponding to albumin, alpha 1 globulin, alpha 2 globulin and gamma globulin. In case of abnormal fractions due to disease, they may be reported with no attempt made for data processing.

SUMMARY OF THE INVENTION

A general objects of the present invention is to provide a method for determining boundary points on densitograms traced on the basis of electrophoresis even when boundary points other than the normal ones are formed on densitograms in simple procedures and high reliability with a computer by determining points on the abscissa corresponding to peak tops on densitograms, adopting these points as standard positions, locating these standard positions on densitograms of unknown samples traced on the basis of electrophoresis, and adopting point having minimum value corresponding to the lowest concentration between each pair of neighboring standard positions as the normal boundary point for calculating an integral of each fraction.

DESCRIPTION OF THE PREFERRED EMBODIMENTS

Now, the boundary point processing method according to the present invention will be described in details below. In the first place, a standard serum such as a commercially available control serum is analyzed by electrophoresis to obtain an electrophoretic pattern having five fractions. Peak top positions and boundary points on the densitogram traced on the basis of the electrophoretic pattern are almost determined depending on type of the carrier used and electrophoretic conditions. Therefore, unknown samples to be analyzed for inspections should show densitograms having development lengths substantially the same as that of the standard serum so long as the type and electrophoretic conditions are kept the same.

Figure 1:
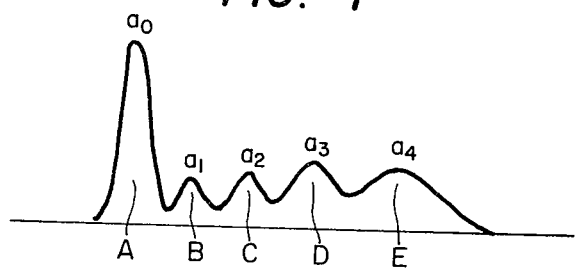
FIG. 1 shows a densitogram illustrating a pattern obtained by electrophoresis of a standard sample.
Figure 2:
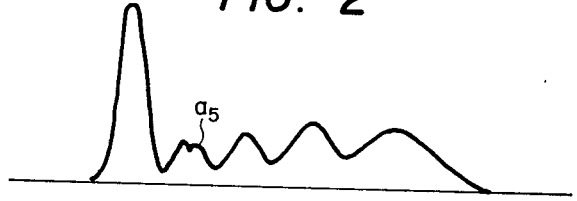
FIG. 2 through FIG. 4 show densitograms illustrating examples of patterns including fractions in addition to the standard fractions.
Figure 3:
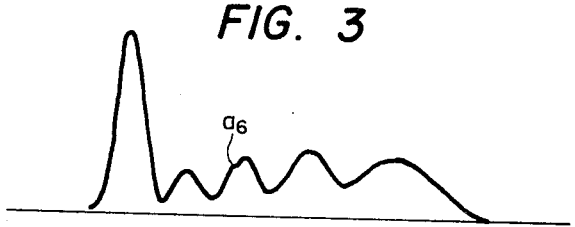
Figure 4:
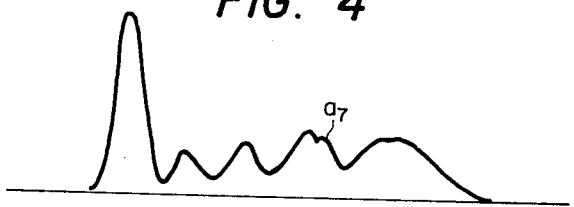
Figure 5:
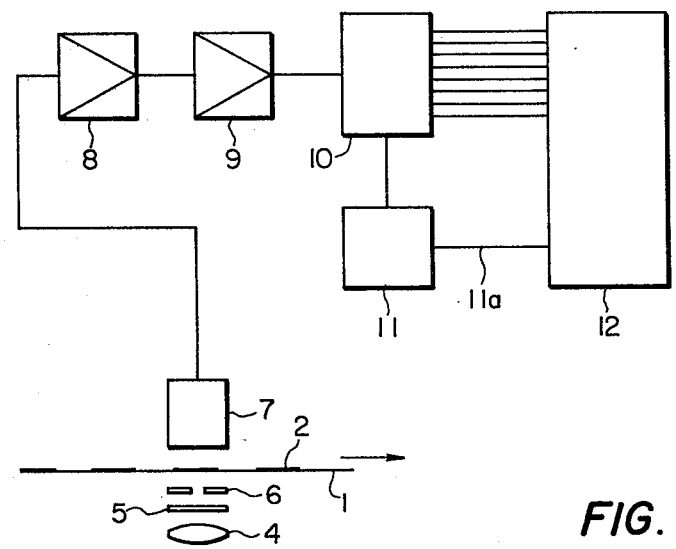
FIG. 5 shows a block diagram illustrating configuration of a system used for processing fractions.
Figure 6:
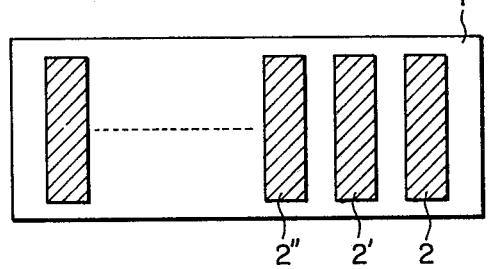
FIG. 6 illustrates a schematic diagram showing a carrier on which fractionated patterns are formed.
Figure 7:
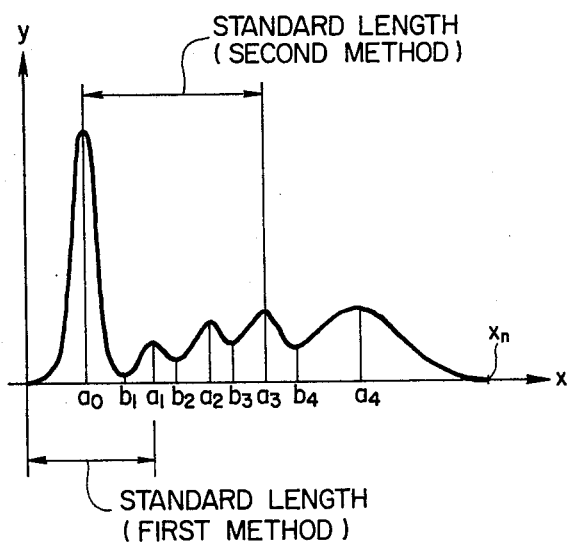
FIG. 7 illustrates a densitogram descriptive of a method to determine positions of peak tops and boundary points on an electrophoretic pattern.

Let us designate the points on the abscissa corresponding to the peak tops by $a_0, a_1, \ldots a_4$ and boundary points by $b_1, b_2, b_3$ and $b_4$ respectively as illustrated in FIG. 7.

Standard lengths (intervals between the individual pairs of neighboring points $a_0$ through $a_4$ and those between the individual pairs of neighboring points $b_1$ through $b_4$) on the densitogram of the standard serum are determined as described below:

A densitogram as shown in FIG. 7 is obtained by photometry of the electrophoretic pattern. Data are sampled from the densitogram at constant time intervals and subjected to A/D conversion for storing concentrations at the sampling points. The sampling points are designated consecutively as $1, 2, 3, \ldots n$ and plotted on the abscissa, and the concentrations at the sampling points are plotted along the ordinate. Based on the stored data, boundary points are to be detected. Let us assume that an optical point on the densitogram has coordinates of $x_b$ and $y_b$. Similarly, neighboring points on the desitogram have coordinates of $x_{b-1}, y_{b-1}$ and $x_{b+1}$ and $y_{b+1}$. Since a boundary point is located at a valley on the densitogram, a boundary point can be determined as $x_b$ which corresponds to a point having an ordinate value of $y_b$ which satisfies the following relation:

$$y_b < y_{b-1}, y_b < y_{b+1}$$

As for abscissa values of the peak top points, $a_0$ should be located between the start point $x_0$ and boundary point $b_1$, $a_1$ between the boundary points $b_1$ and $b_2$, $a_2$ between the boundary points $b_2$ and $b_3$, and $a_4$ between the boundary points $b_4$ and end point $x_n$. In the procedures similar to those used for determining the boundary points, $a_0$ through $a_4$ can be determined as $x_a$ corresponding to points on the densitogram which have $y_a$ values satisfying the following relation:

$$y_a > y_{a-1}, y_a > y_{a+1}$$

The x values of $b_1, b_2, \ldots$ and $a_0, a_1, \ldots$ thus determined are proportional to the lengths as measured from the start point $x_0$ to the points themselves (lengths along the abscissa) in a relationship of 1:1. It is therefore possible to use a scale of constant time intervals (sampling intervals) in place of the length as measured from the start point.

A fraction of prealbumin is usually traced before (on the side of the start point) the fraction of albumin, and generally processed as a portion of the latter fraction. By the method according to the present invention, the prealbumin fraction is processed as a portion included in the albumin fraction and the first fraction is therefore processed as albumin fraction. The concentration represented by the prealbumin peak is far lower than the concentration represented by the albumin peak. It is therefore possible to process the prealbumin fraction as a portion included in the albumin fraction by setting an adequate concentration level which is lower than the concentration represented by the albumin peak but higher than the concentration represented by the prealbumin peak, and adopting no boundary point until a peak exceeding the preset level appears. The boundary points on the densitogram of the standard serum are determined as described above.

Successively, individual boundary points (valleys) on a densitogram obtained on the basis of electrophoresis of an unknown sample are to be determined in the procedures similar to those used for determining the boundary points on the densitogram of the standard serum.

Figure 8:
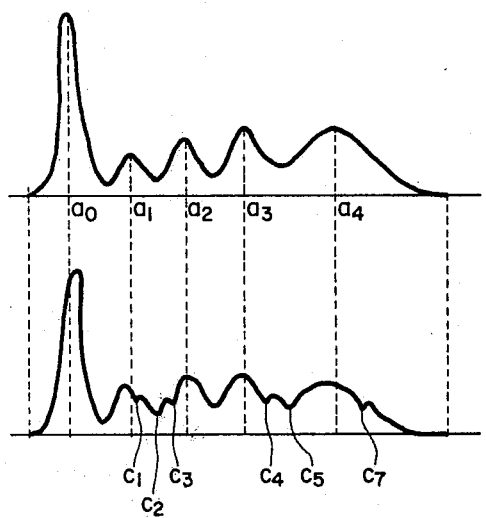
FIG. 8 illustrates densitograms descriptive of a first embodiment of the processing method according to the present invention.

Using the $a_0, a_1, a_2$ and $a_3$ determined on the densitogram of the standard serum as standard points as shown in FIG. 8, they are located on the densitogram of the unknown sample. Number of boundary points is counted in each of the sections $a_0$-$a_1$, $a_1$-$a_2$, $a_2$-$a_3$ and $a_3$-$a_4$. When the number of boundary point is counted as 1, it is adopted as a normal boundary point. When two or more boundary points are counted, the one corresponding to the lowest concentration is adopted as a normal one and the others are erased. In FIG. 8, for example, only one boundary point exists in each of the sections $a_0$-$a_1$ and $a_2$-$a_3$, and these points are adopted as the first and third boundary points respectively. In the section $a_1$-$a_2$, three boundary points of $c_1, c_2$ and $c_3$ exist and the one corresponding to the lowest concentration is adopted as the second boundary point. In the section of $a_3$-$a_4$, two boundary points of $c_4$ and $c_5$ are detected, and the one corresponding to the lower concentration is adopted as the fourth boundary point. All boundary points detected after $a_4$ (for example, $c_7$ shown in FIG. 8) are erased. Boundary points due to beta lipoprotein, $beta_{lc}$ protein and foreign matters always correspond to concentrations higher than those corresponding to the normal boundary points. Therefore, the above-described processing method is capable of correctly processing boundary points by erasing boundary points other than the normal ones. In data processing by the above-described method, positional relation between the photometric apparatus and electrophoretic patterns may be varied for individual carriers due to deviation in setting the carriers, applied positions of sera and so on, thereby deviating the start point $x_0$ on densitograms. Such deviation is undesirable since it makes percentage of integral till the first boundary point or that after the fourth boundary point inaccurate. As a boundary point processing method capable of eliminating such influence, the present invention provide a second method described below:

In the first place, the points corresponding to the peaks on the densitogram of a standard serum are determined in the procedures already described above. Taking the point corresponding to the albumin peak top ($a_0$ determined by the first method) as the origin, the distances from the origin to $a_1, a_2, a_3$ and $a_4$ respectively are stored as x values. In this case, conversion of $a_0 \rightarrow 0$, $a_1 \rightarrow a_1 - a_0$, $a_2 \rightarrow a_2 - a_0$, $a_3 \rightarrow a_3 - a_0$ and $a_4 \rightarrow a_4 - a_0$ is performed for computation.

Successively, a point corresponding to the albumin peak top on a densitogram of an unknown sample is detected. Taking the point as the origin, $a_0, a_1, a_2, a_3$ and $a_4$ determined on the densitogram of the standard serum are located on the densitogram of the unknown sample. Then, number of boundary points in each of the sections $a_0$-$a_1$, $a_1$-$a_2$, $a_2$-$a_3$ and $a_3$-$a_4$ is counted. When a single boundary point is detected, it is adopted as the normal one. If two or more boundary points are detected, the one corresponding to the lowest concentration is adopted as the normal one, while all the other boundary points are erased. Therefore, these procedures permit setting the points corresponding to the first peak tops on both the densitograms of the standard serum and unknown sample at the origin and determining correct integrals of the individual fractions even when the start point is deviated.

Even when abnormal boundary points are formed due to substances insensible of electrophoresis and remaining at the applied position, beta globulin and beta lc globulin as well as contamination of electrophoretic patterns and electric noise, the two methods described above permit distinguishing the normal boundary points from abnormal ones corresponding to higher concentrations so as to select only one boundary point between each pair of succeeding standard points and processing all densitograms so as to have five normal boundary points.

Figure 9:
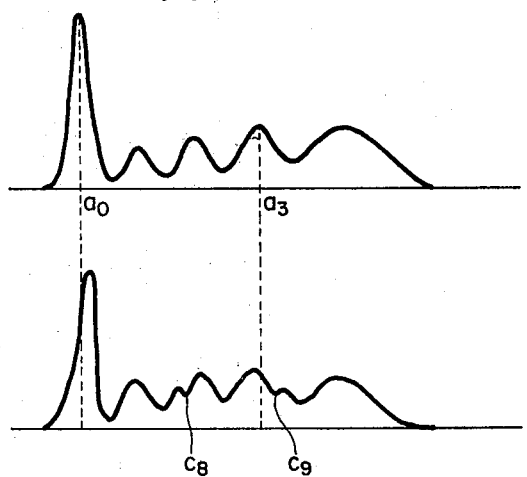
FIG. 9 shows densitograms descriptive of a third embodiment of the processing method according to the present invention.

However, abnormal boundary points due to substance insensible of electrophoresis and remaining at the applied position, contamination of electrophoretic patterns, electric noise, etc. are formed rather rarely and negligible in practice. For electrophoresis of man's sera, it is therefore possible to adopt a third simplified method described below:

In the first place, analytical data of a standard sample are processed in the same procedures as those of the first or second method. Successively, $a_0$ corresponding to the peak of the first fraction and $a_3$ corresponding to the peak of the fourth fraction on the densitogram of the standard sample are located on the densitogram of an unknown sample. Number of boundary points existing between $a_0$ and $a_3$ is counted. When three boundary points are detected, they are adopted as the normal boundary points. If four boundary points are detected, it is considered that one of the boundary points has been formed due to beta lipoprotein ($c_8$ in FIG. 9) and, therefore the second boundary point as counted from the side of $a_3$ is erased. When a single boundary point is detected in the section after $a_3$, it is adopted as the normal boundary point. If two boundary points are detected in this section ($c_9$ in FIG. 9), it is considered that one of them has been formed due to beta lc globulin and the one on the side of $a_3$ is erased. The third method described above permits processing a densitogram into correct five fractions by erasing abnormal boundary points due to beta lipoprotein and beta lc globulin so long as boundary points due to substances insensible of electrophoresis and remaining at the applied position as well as electric noise are negligible.

In addition, the second processing method is compatible with the processing made setting the origin at the point on the abscissa corresponding to the first peak top adopted for the second processing method.

As is understood from the foregoing descriptions, the processing method according to the present invention makes it possible to automatically process densitograms of unknown samples into five normal fractions even when they have five or more boundary points according to a computer program for automatic measurements and recording of percentages of integrals of the individual fractions. The second method according to the present invention permits determining correct percentages of integrals of the individual fractions regardless of positional deviation on the carrier. Moreover, the third method according to the present invention simplifies data processing procedures by minimizing number of the standard positions to be located on densitograms of unknown samples.

We claim:

1. A method for determining boundary points in electrophoresis comprising a step to determine points on the abscissa corresponding to peak tops on a densitogram traced based on electrophoresis and select said points as standard positions, a step to locate said standard positions on a densitogram of an unknown sample traced based on electrophoresis of an unknown sample, a step to count number of points having minimum values existing between each pair of the neighboring standard positions on the densitogram of the unknown sample and a step to select the point having the minimum value as the normal boundary point when a single point is counted or the one corresponding to the lowest concentration as the normal boundary point when 2 or more points are counted.

2. A method for determining boundary points in electrophoresis according to claim 1 so adapted as to erase all points which have minimum values and located outside the range from the first standard position to the last standard position.

3. A method for determining boundary points in electrophoresis according to claim 1 so adapted as to erase the boundary point formed due to prealbumin by presetting a concentration level lower than that corresponding to the peak of albumin fraction and higher than that corresponding to the peak of prealbumin fraction, and selecting a first peak exceeding the preset level as the first normal peak.

4. A method for determining boundary points in electrophoresis according to claim 1 so adapted as to carry out processing after coinciding the albumin peak on densitogram of said unknown sample with that on densitogram of said standard sample.

5. A method for determining boundary points in electrophoresis comprising a step to determine points corresponding to peak tops on the abscissa on densitogram traced on the basis of electrophoresis of a standard sample and select said points as standard positions, a step to locate said standard positions on a densitogram of an unknown sample traced on the basis of electrophoresis, a step to count number of points having minimum values and located between the first and fourth of the standard positions located on the densitogram of said unknown sample, a step to select all the points having minimum values as the normal boundary points when three points are counted or all the points having minimum values except for the second one which is counted from the side of the fourth standard position as the normal boundary points when four points are counted, a step to count number of points having minimum values and located after the fourth standard point and a step to adopt the point having minimum value as the normal boundary point when a single point is counted or the point having minimum value and located farther from the fourth standard point as the normal boundary point when two points are counted.

* * * * *